United States Patent
Zocchi et al.

(10) Patent No.: US 7,786,042 B2
(45) Date of Patent: Aug. 31, 2010

(54) FLURIDONE AS AN ANTI-INFLAMMATORY AGENT

(75) Inventors: Elena Zocchi, Genoa (IT); Lucrezia Guida, Genoa (IT); Santina Bruzzone, Arenzano (IT); Sonia Scarfi', Genoa (IT); Mirko Magnone, Genoa (IT); Giovanna Basile, Genoa (IT); Umberto Benatti, Genoa (IT); Antonio De Flora, Genoa (IT); Iliana Moreschi, Albisola Superiore (IT); Luisa Franco, Genoa (IT); Annalisa Salis, Quiliano (IT)

(73) Assignee: Universita' Degli Studi Di Genova, Genoa (IT)

( * ) Notice: Subject to any disclaimer, the term of this patent is extended or adjusted under 35 U.S.C. 154(b) by 0 days.

(21) Appl. No.: 12/089,203

(22) PCT Filed: Oct. 6, 2006

(86) PCT No.: PCT/IB2006/053669

§ 371 (c)(1),
(2), (4) Date: Apr. 3, 2008

(87) PCT Pub. No.: WO2007/042983

PCT Pub. Date: Apr. 19, 2007

(65) Prior Publication Data

US 2008/0242705 A1 Oct. 2, 2008

(30) Foreign Application Priority Data

Oct. 7, 2005 (IT) .......................... TO2005A0708

(51) Int. Cl.
*A01N 43/34* (2006.01)
*A61P 29/00* (2006.01)
*A61K 31/44* (2006.01)

(52) U.S. Cl. .................. 504/155; 514/367; 514/886; 504/255; 504/121

(58) Field of Classification Search ................ 504/155, 504/345, 121, 367; 514/886, 345
See application file for complete search history.

(56) References Cited

U.S. PATENT DOCUMENTS 3,958,025 A 5/1976 Livingston (Continued)

FOREIGN PATENT DOCUMENTS

EP 0 240 257 A2 10/1987

(Continued)

OTHER PUBLICATIONS

PCT International Search Report for PCT/IB2006/053669 filed on Oct. 6, 2006 in the name of Universita' Degli Studi Di Genova, et al.

(Continued)

*Primary Examiner*—Ardin Marschel
*Assistant Examiner*—Savitha Rao
(74) *Attorney, Agent, or Firm*—Steinfl & Bruno

(57) ABSTRACT

The invention relates to a novel use of fluridone—compound known per se and used as an aquatic erbicide—in the medical field, in particular as an active compound for preparing a medicament having anti-inflammatory activity. Pharmaceutical compositions comprising fluridone as an active compound and pharmaceutically acceptable carriers and/or diluents are also disclosed. Finally, there is disclosed the pro-inflammatory activity of abscisic acid (ABA), a plant hormone which is also found in mammal serum and against which fluridone acts an inhibitor.

13 Claims, 8 Drawing Sheets

U.S. PATENT DOCUMENTS

Figure 1:
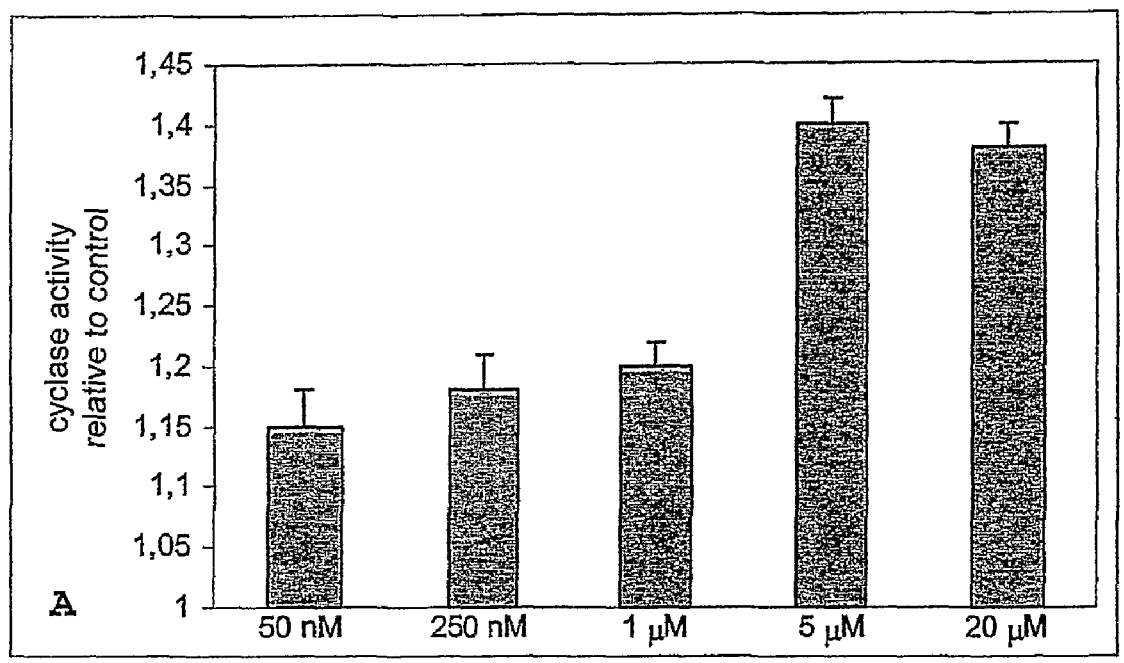
Figure 1:
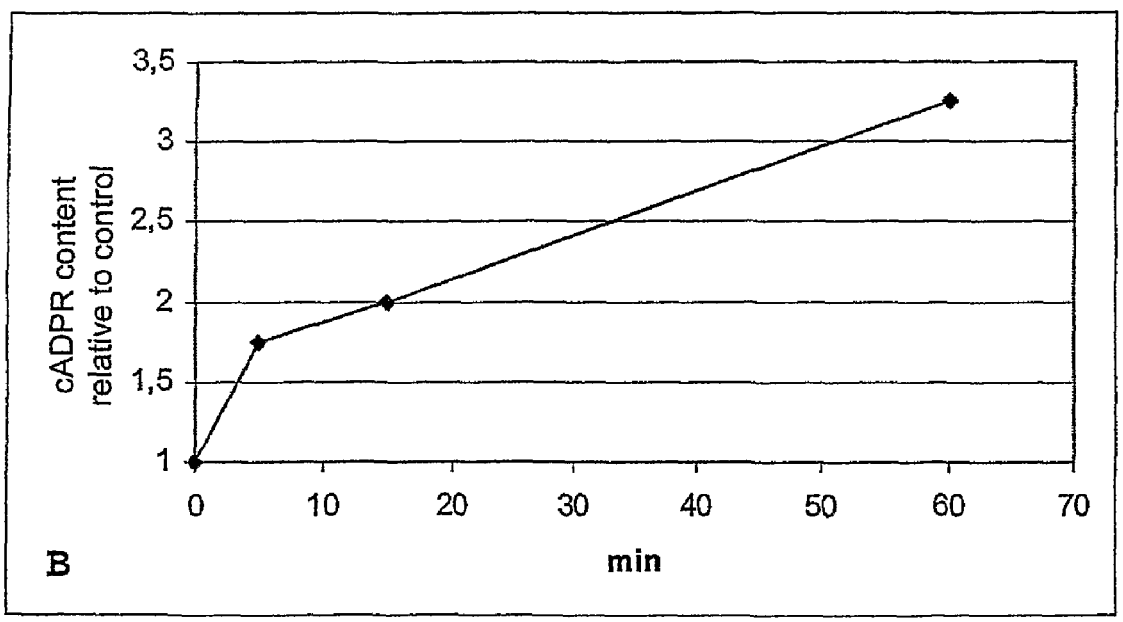

2002/0032235 A1* 3/2002 Schrier et al. ............... 514/561
2004/0117125 A1   6/2004 Chen et al.

FOREIGN PATENT DOCUMENTS

WO   WO 98/48808   11/1998

OTHER PUBLICATIONS

PCT Written Opinion for PCT/IB2006/053669 filed on Oct. 6, 2006 in the name of Universita' Degli Studi Di ,Genova, et al.

* cited by examiner

FLURIDONE AS AN ANTI-INFLAMMATORY AGENT

CROSS REFERENCE TO RELATED APPLICATIONS

This application is the national phase of International Application PCT/IB2006/053669 filed on Jun. 10, 2006 which, in turn, claims priority to Italian Patent Application TO2005A000708 filed on Oct. 7, 2005.

The present invention relates to a new anti-inflammatory agent and to pharmaceutical compositions comprising said new anti-inflammatory agent.

The prior art discloses several effective anti-inflammatory agents, for example steroid anti-inflammatory drugs (cortisone and derivatives thereof) and non-steroid anti-inflammatory drugs (acetylsalicylic acid, indometacin, ibuprofen, ketoprofen, diclofenac, naproxen, piroxicam, etc.).

However, the majority of these agents may have side effects, for instance at the gastrointestinal, renal, cardiovascular, hepatic and respiratory level, and may produce adverse reactions.

For this reason, the discovery of new anti-inflammatory agents lacking the side effects of known drugs is desirable, particularly if they demonstrate good anti-inflammatory activity, low toxicity and a broad spectrum of activity.

Identification of new anti-inflammatory agents may be helpful to increase our ability to tackle the problem of the side effects of the most commonly used anti-inflammatory drugs.

The present inventors have now found that a derivative of 4-pyridone known per se, fluridone, shows surprisingly good anti-inflammatory properties and satisfies the above-mentioned requirements, particularly the wide spectrum of activity.

Fluridone is a compound known per se which, as far as the inventors know, has been used until now only in agriculture as an herbicide.

The inventors are not aware of any previously known pharmacological activity of fluridone on humans or on animals, nor of any medicinal utilisation of the compound. Fluridone is a compound with the formula:

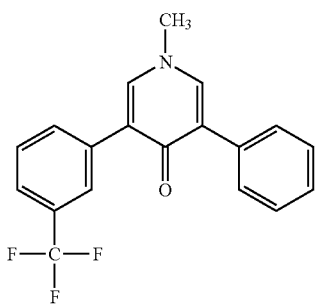

(IUPAC name: 1-methyl-3-phenyl-5-($\alpha,\alpha,\alpha$-trifluoro-m-tolyl)-4-pyridone; CAS no 59756-60-4). This compound has been utilised since the second half of the Eighties as an herbicide (with the commercial name "Sonar"), particularly to eliminate aquatic plant growth in lakes, water reservoirs and irrigation channels. The documented absence of adverse effects on animals, including fish, mammals and birds, has enabled the American Environmental Protection Agency (EPA) to authorise its use in the field. In-depth studies on laboratory animals (mice, rats, dogs, fish and birds) which have demonstrated the absence of toxic, mutagenic, teratogenic or cancerogenic effects of fluridone, even at high concentrations, have been carried out. The $LD_{50}$ in rats by oral administration is >10 g/Kg. Based on the results of experiments on chronic toxicity in rats fed with fluridone, and applying a dose reduction of two logarithms as a measure of further safety, the maximum permissible intake allowed in humans is 4.8 mg/Kg/day.

The mechanism of fluridone toxicity on plants depends on its ability to inhibit the enzyme fitoene desaturase, which catalyses one of the first steps of the biosynthetic pathway of β-carotene, the precursor of abscisic acid (ABA). The toxic effect on plants is due only to a minor extent to the inhibition of ABA synthesis, although this hormone plays essential roles in plants, among them the regulation of seed development and germination, and is primarily due to the inhibition of carotenoid biosynthesis, which have a protective effect on chlorophyll against phototoxicity (by absorbing part of the light energy and protecting against oxidative damage due to oxygen radicals).

As illustrated in more detail in the experimental section of the present patent application, the invention is based on studies performed by the inventors regarding the effects of fluridone and of ABA on various human and murine inflammatory cell types. As known from plant biology, fluridone is an inhibitor of ABA synthesis in plants.

The studies performed indicate that fluridone at micromolar concentrations is capable of exerting anti-inflammatory effects on several human (granulocytes, lymphocytes, monocytes) and murine (macrophages and microglia) cell types. Furthermore, it has been ascertained that ABA is present not only in higher plants, in Porifera and in Hydrozoa, as previously described, but also in human plasma and in some types of human inflammatory cells, where its concentration is modulated by several inflammatory stimuli and where it exerts a stimulation of cellular pro-inflammatory activities. In the light of the pro-inflammatory effect of ABA on human inflammatory cells, it is possible to envisage the usefulness of ABA as an active compound in a medicament capable of stimulating the pro-inflammatory functions of inflammatory cells, particularly human lymphocytes, granulocytes and monocytes, for the treatment of pathological conditions in which the specific functions of these cells are deficient. This deficiency of the inflammatory functions may result from congenital (as in chronic granulomatous disease) or from acquired (as in chronic viral infections) causes.

Finally, the studies performed indicate that exogenously added fluridone reduces both the ABA content and the production of other known pro-inflammatory cytokines in inflammatory cells, suggesting that fluridone may exert useful broad-spectrum anti-inflammatory effects.

A first aspect of the present invention is therefore the use of abscisic acid (ABA) for preparing a medicament for the treatment of pathological conditions characterised by a deficit in the specific functions of inflammatory cells.

In the present description, the expression "abscisic acid" or "ABA" refers to the compound I' (±)-cis, trans ABA having the following structural formula:

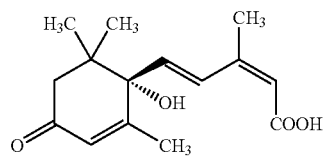

The experiments performed have demonstrated that ABA shows a pro-inflammatory effect at micromolar concentrations, preferably comprised between 0.1 and 50 μM, and even more preferably between 5 and 20 μM. These ABA concentrations may be used "in vitro" to treat cells purified from patients' blood prior to reinfusion. Alternatively, ABA may be directly infused "in vivo" into the site of infection so that it can exert its chemotactic and pro-inflammatory action in situ.

A second aspect of the present invention is the use of fluridone as an active compound in a medicament, in particular the use of fluridone for preparing a medicament having anti-inflammatory activity.

Another aspect of the invention is a pharmaceutical composition comprising a pharmacologically effective amount of fluridone and a pharmacologically acceptable carrier or diluent.

The pharmaceutical composition of the invention may be prepared in a form suitable for systemic administration, e.g. oral, intravenous, intramuscular, subcutaneous, rectal, intradermal, nasal, tracheal, bronchial or topical. To this purpose, the composition may be prepared in a dosage form such as tablets, capsules, vials, suppositories, injectable solutions or suspensions, creams, lotions, colluttories, powders, solutions etc., with conventional preparation methods and excipients which are well known to the person skilled in the art, e.g. with the use of conventional ligands, carriers, diluents, fillers, extending agents, emulsifying agents, solvents suitable for the selected dosage form.

The experiments performed indicate that fluridone shows an anti-inflammatory effect at nano/micromolar concentrations, preferably at concentrations comprised between 250 nM and 50 μM, more preferably between 5 and 20 μM.

An effective concentration of fluridone may be reached in humans through administration of amounts comprised between 1 and 50 mg/Kg, depending on the specific conditions, both with reference to the illness to be treated and with reference to the condition and type of patient.

The experimental section which follows is provided to further illustrate the invention without any intent of limitation. In this experimental section reference is made to the following attached drawings, wherein:

FIG. 1 shows the effects of ABA on the GDP-ribosyl cyclase activity and on the content of cyclic ADP-ribose (cADPR) in human granulocytes. Panel A. GDP-ribosyl cyclase activity has been measured in granulocytes in the presence of increasing ABA concentrations, added together with the cyclase substrate NGD$^+$. The results are expressed as cyclase activity relative to control cells, incubated in the absence of ABA (mean ±SD from 5 determinations). Panel B. The intracellular concentration of cADPR was measured by enzymatic cycling assay (Materials and Methods) on granulocytes incubated with 20 μM ABA for the periods of time indicated. The results are expressed as [cADPR]$_i$ relative to control cells, incubated without ABA (n=2).

Figure 2:
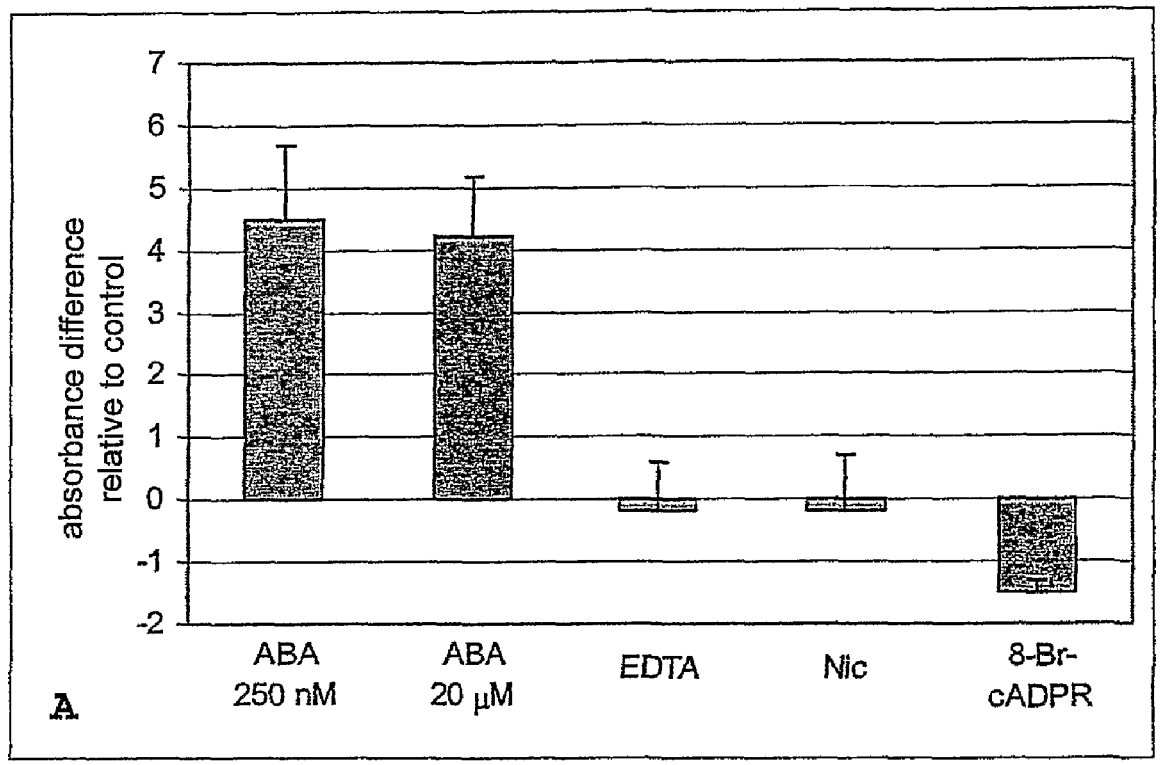
Figure 2:
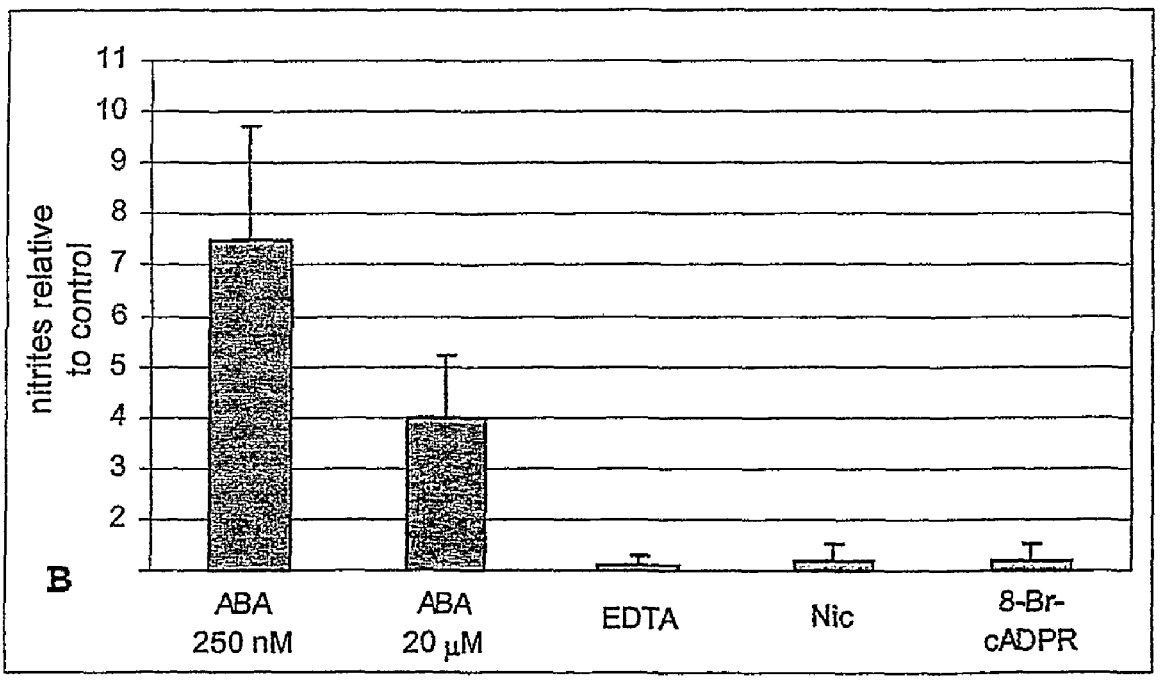

FIG. 2 shows the effects of ABA on the production of reactive oxygen radicals (ROS) and NO by human granulocytes. Granulocytes were resuspended at 5×10$^6$/ml in HBSS and 225 μl of the cell suspension were added to 50 μl of 0.2 mM cytochrome c and were incubated for 30 min at 37° C. in the absence (control) or in the presence of 250 nM or 20 μM ABA, the latter concentration without or with 1 mM EDTA, 20 mM nicotinamide or 0.1 mM 8-Br-cADPR. The amount of ROS (panel A) or of NO (panel B) in the cell supernatant was measured as described in Materials and Methods. The results are expressed as the production relative to control cells, not stimulated with ABA, and are the mean ±SD from 5 experiments.

Figure 3:
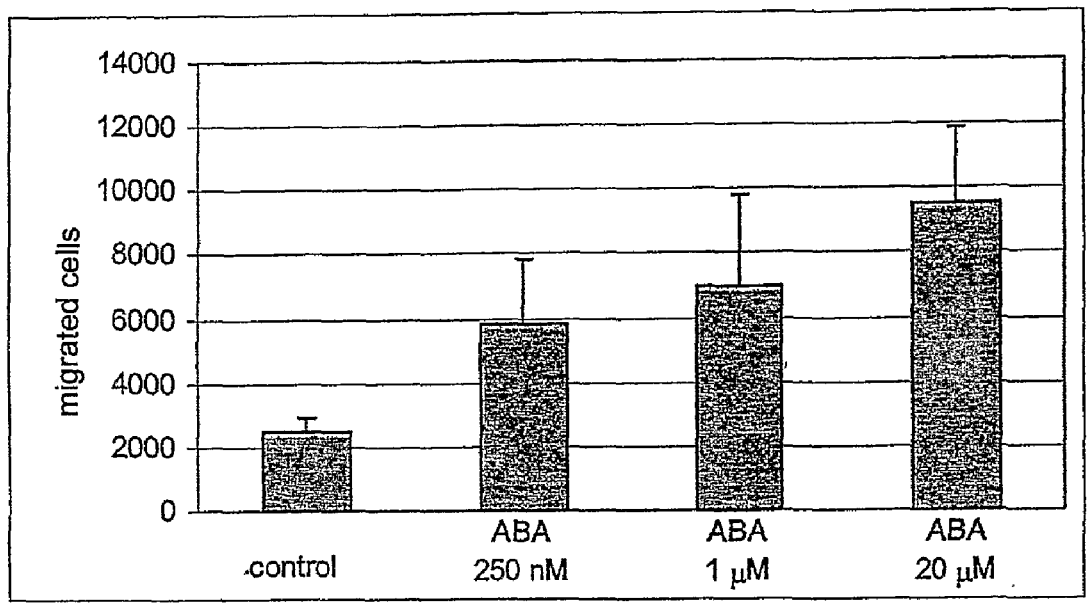

FIG. 3 shows the chemoattractant effect of ABA on human granulocytes. Migration of granulocytes across porous membranes (3 μM) towards buffer (control) or towards increasing concentrations of ABA was evaluated as described under Materials and Methods. The results are expressed as the absolute number of cells migrated across the membrane and are the mean ±SD from 5 experiments.

Figure 4:
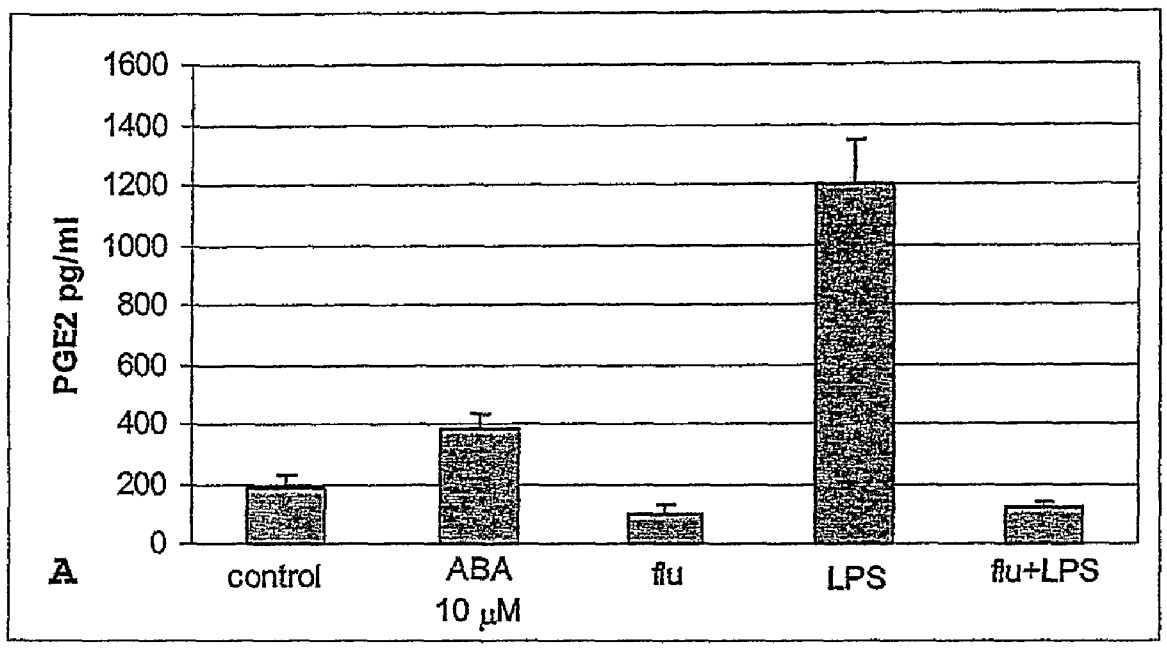
Figure 4:
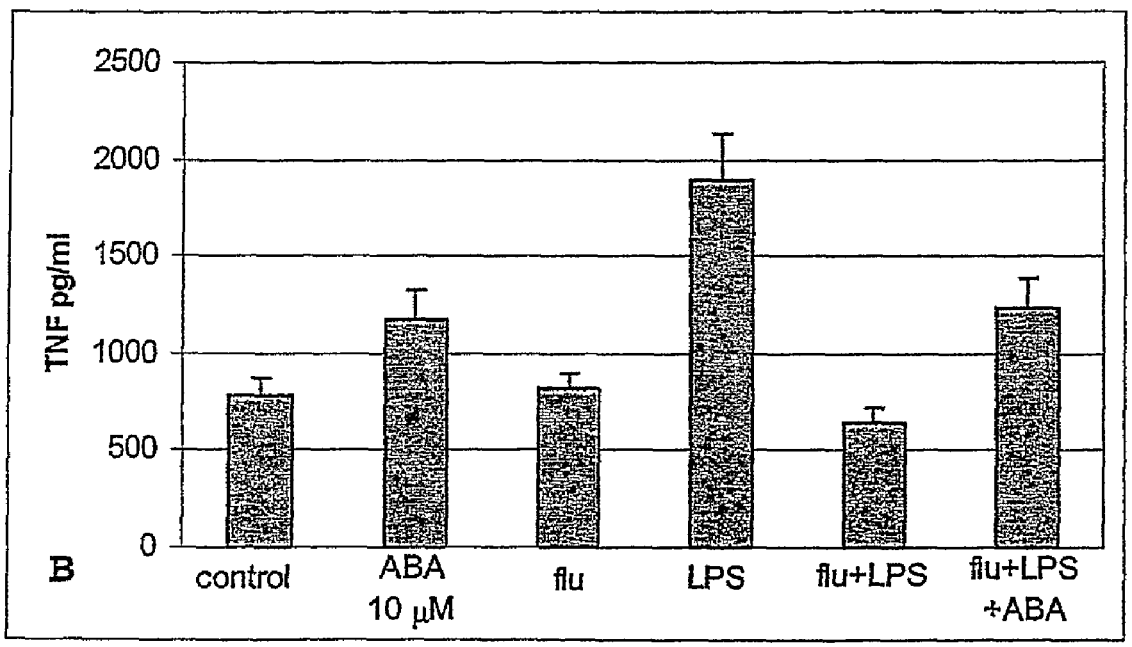

FIG. 4 shows the effects of ABA and of fluridone on the production of PGE$_2$ and TNF-α by human monocytes. Human monocytes were pre-incubated with 50 μM fluridone (flu) for 2 hours and then stimulated with 10 μM ABA or with 100 ng/ml of lipopolysaccharide (LPS) for 6 hours. The concentration of PGE$_2$ (panel A) and of TNF-α (panel B) in the cell supernatant was measured as described under Materials and Methods and compared with that of untreated cells (control). The results are the mean ±SD from 4 experiments.

Figure 5:
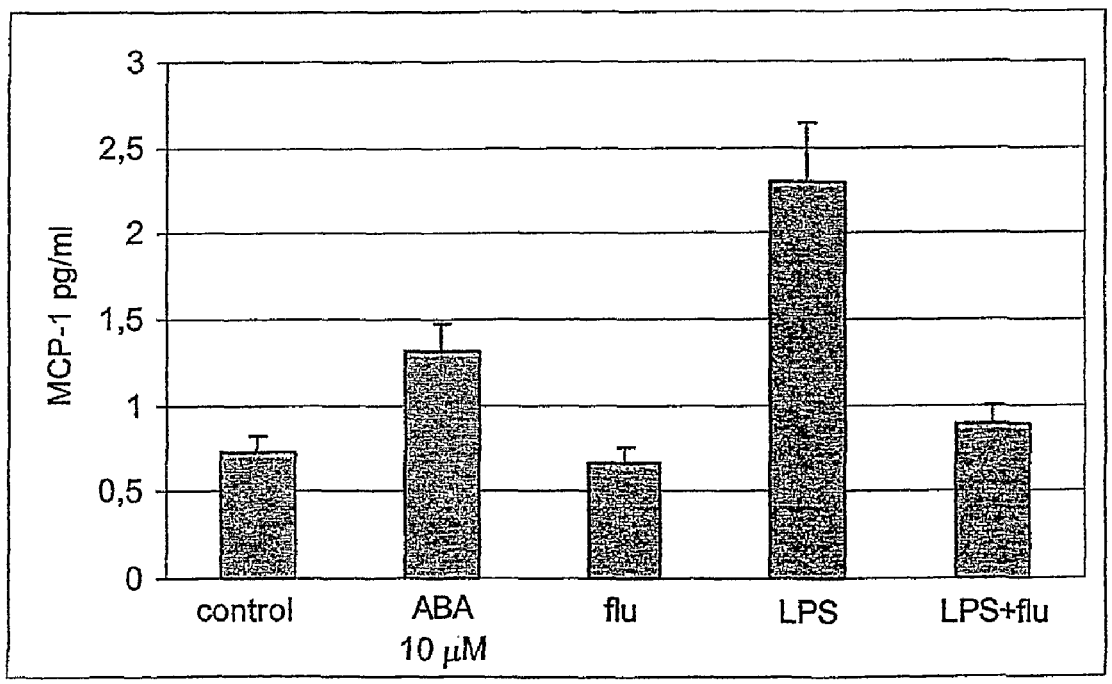

FIG. 5 shows the effects of ABA and of fluridone on MCP-1 release from human monocytes. Human monocytes were incubated for 6 hours with 10 μM ABA or with 100 ng/ml of lipopolysaccharide (LPS), in the presence or in the absence of fluridone (50 μM) and the MCP-1 concentration in the cell supernatant was immunoenzimatically measured, with a commercially available kit (R&D System, CA, USA). The results are the mean ±SD from 3 experiments.

Figure 6:
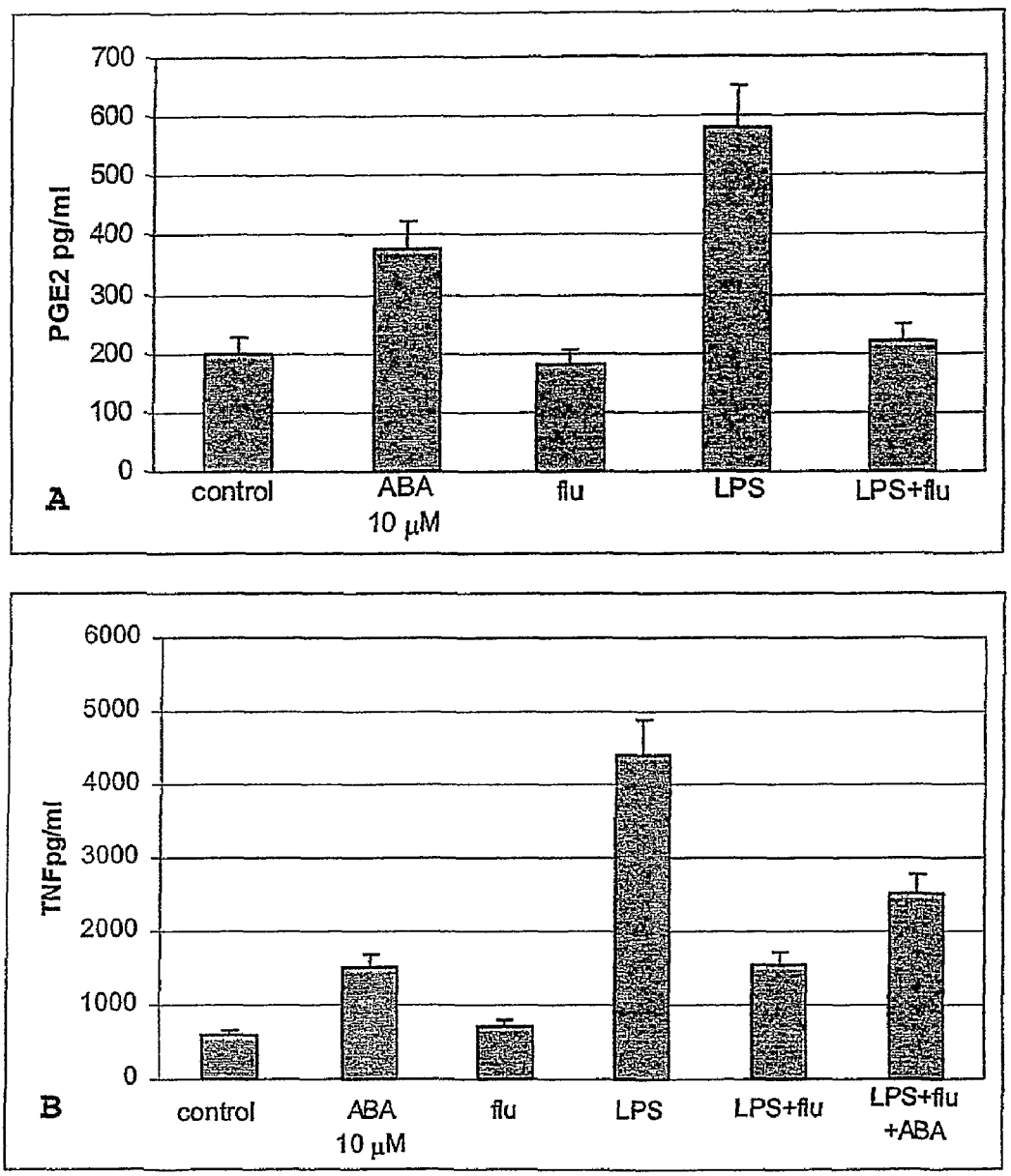

FIG. 6 shows the effects of ABA and of fluridone on the production of PGE$_2$ and of TNF-α by murine macrophages. Murine macrophages of the continuous cell line RAW 264.7 were pre-incubated with 50 μM fluridone (flu) for 2 hours and then stimulated with 10 μM ABA or with 100 ng/ml of lipopolysaccharide (LPS) for 6 hours. The concentration of PGE$_2$ (panel A) or of TNF-α (panel B) in the cell supernatant was measured as described under Materials and Methods and was compared with that from untreated (control) cells. The results are the mean ±SD from 4 experiments.

Figure 7:
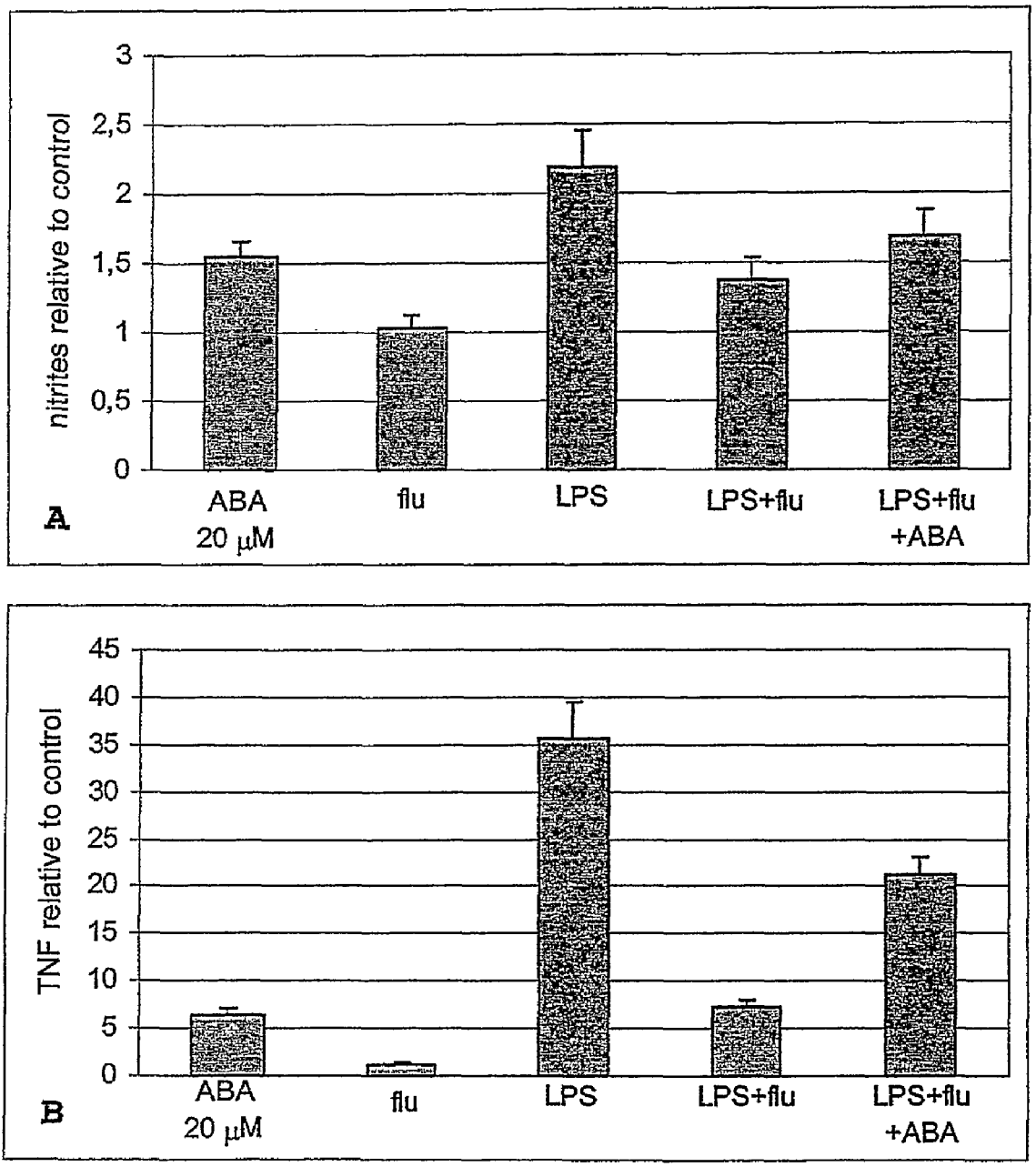

FIG. 7 shows the effects of ABA and of fluridone on the production of PGE$_2$ and of TNF-α by murine microglia. Confluent cell cultures from the murine microglia cell line N9 were pre-incubated in the presence or in the absence of 50 μM fluridone for 4 hours and then stimulated with 10 μM ABA or with 100 ng/ml lipopolysaccharide for 24 hours. The concentration of PGE$_2$ (panel A) and of TNF-α (panel B) in the cell supernatant was measured as described under Materials and Methods. The results are expressed as release relative to control cultures in the absence of added stimuli and are the mean ±SD from 4 experiments.

Figure 8:
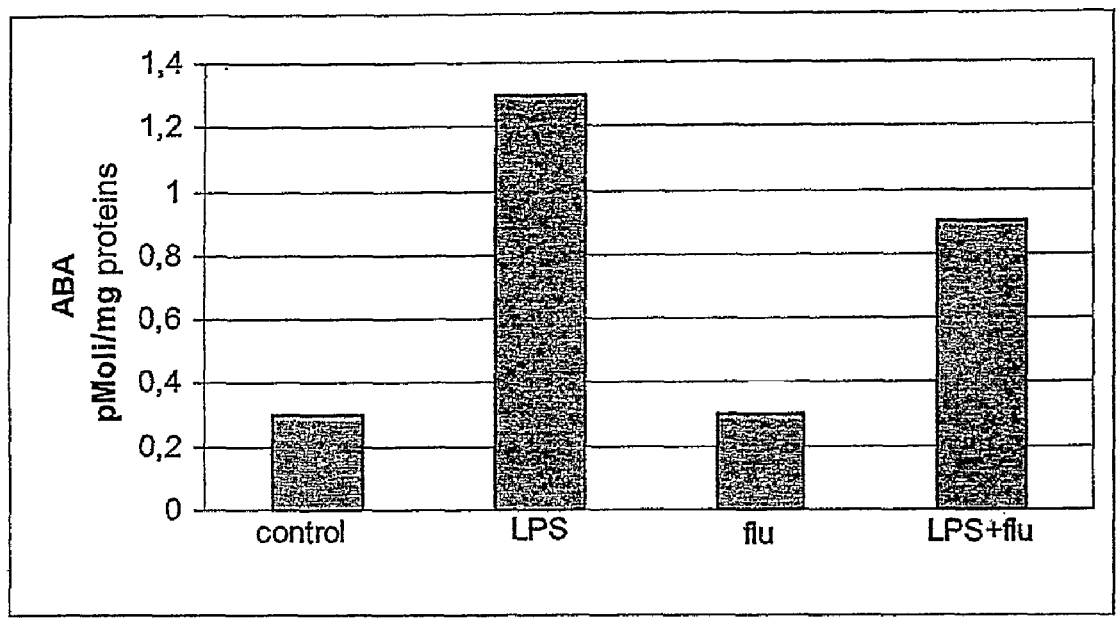

FIG. 8 shows the ABA content in murine microglia cells. Cells from the murine microglial cell line N9 were pre-incubated with or without 50 μM fluridone for 2 hours and then stimulated with 100 ng/ml lipopolysaccharide (LPS) for 24 hours. The ABA content was measured by HPLC-MS (see Materials and Methods) and was compared with that of untreated cells (control). The results are the mean from 2 experiments.

Figure 9:
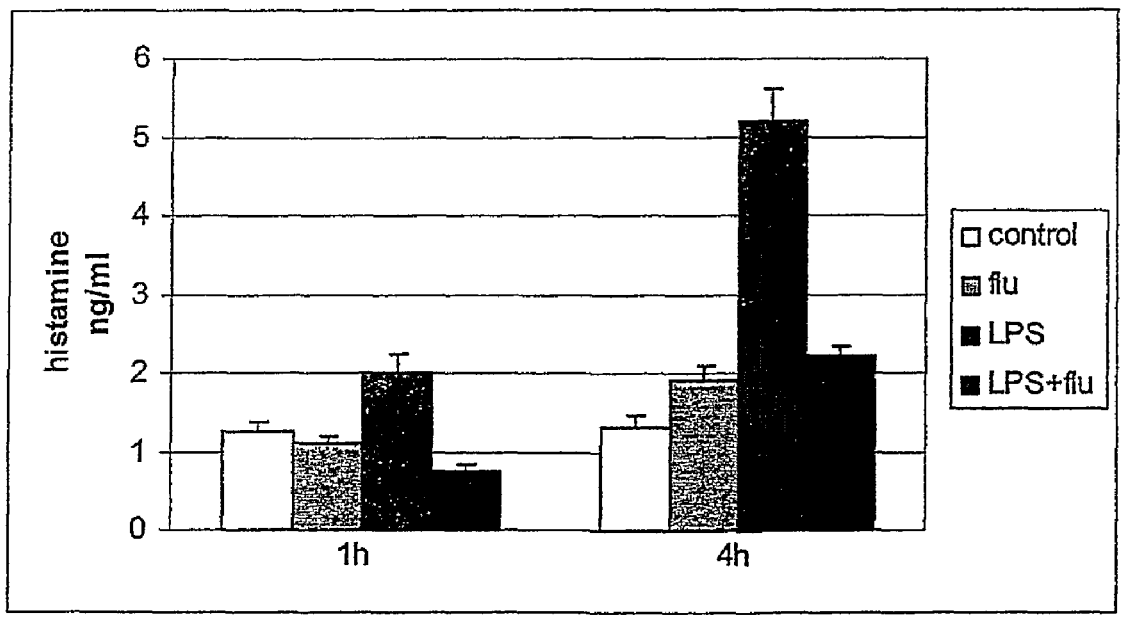

FIG. 9 shows the effect of fluridone on the LPS-induced histamine release from blood cells. Whole blood was pre-incubated for 2 hours at 25° C. in the absence (control) or in the presence of 50 μM fluridone. Then, 100 ng/ml of lipopolysaccharide (LPS) was added to the blood at 37° C. for the time indicated. The histamine concentration in plasma was measured immunoenzymatically with a commercially available kit (IBL-Hamburg, Germany). The results are the mean ±SD from 3 experiments.

Figure 10:
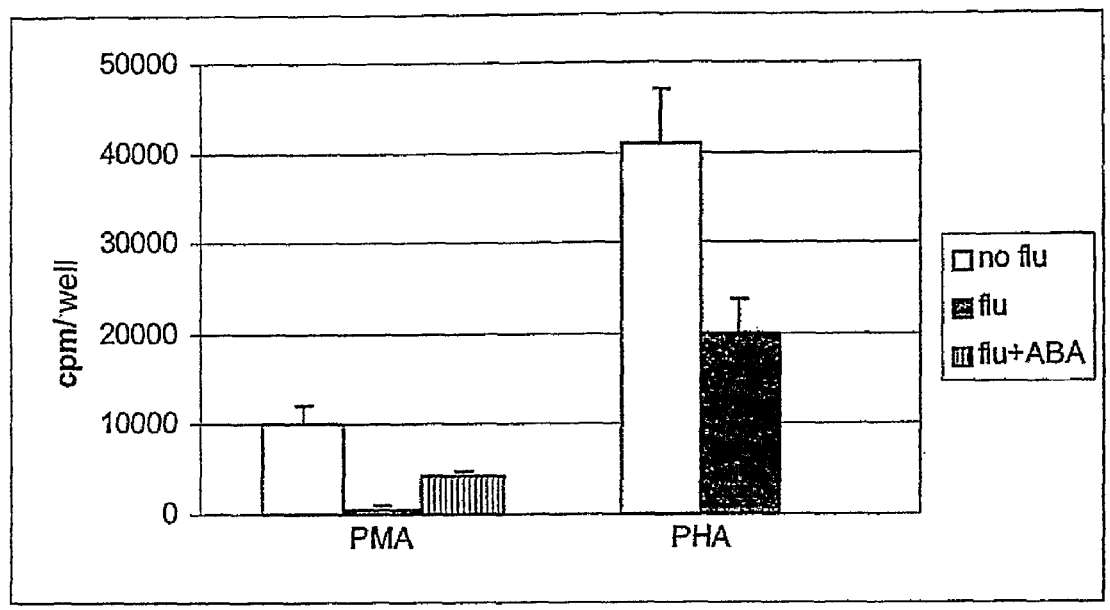

FIG. 10 shows the effects of fluridone on the lymphocyte proliferation stimulated by PMA or PHA. Low density mononuclear cells (lymphocytes and monocytes), isolated from peripheral blood, were incubated in triplicate (1.5×10$^5$/well) in 96-well plates in RPMI containing 20% autologous plasma in the absence (control) or in the presence of 50 µM fluridone for 18 hours. Phytohemagglutinin (PHA) (0.1 µg/ml) or phorbol myristate acetate (PMA) (0.1 µg/ml) were then added, with or without the simultaneous addition of ABA. After 72 hours, [$^3$H]-Thymidine (Amersham Biosciences, Uppsala, Sweden) was added to the cultures (0.2 µCi/well) and after 6 hours the incorporated radioactivity was evaluated by filtration of the cells on glass fiber filters (Whatman, Maidenstone, UK). Results are the mean ±SD from 3 experiments. In the absence of stimuli (PHA or PMA), no lymphocyte proliferation was observed.

Figure 11:
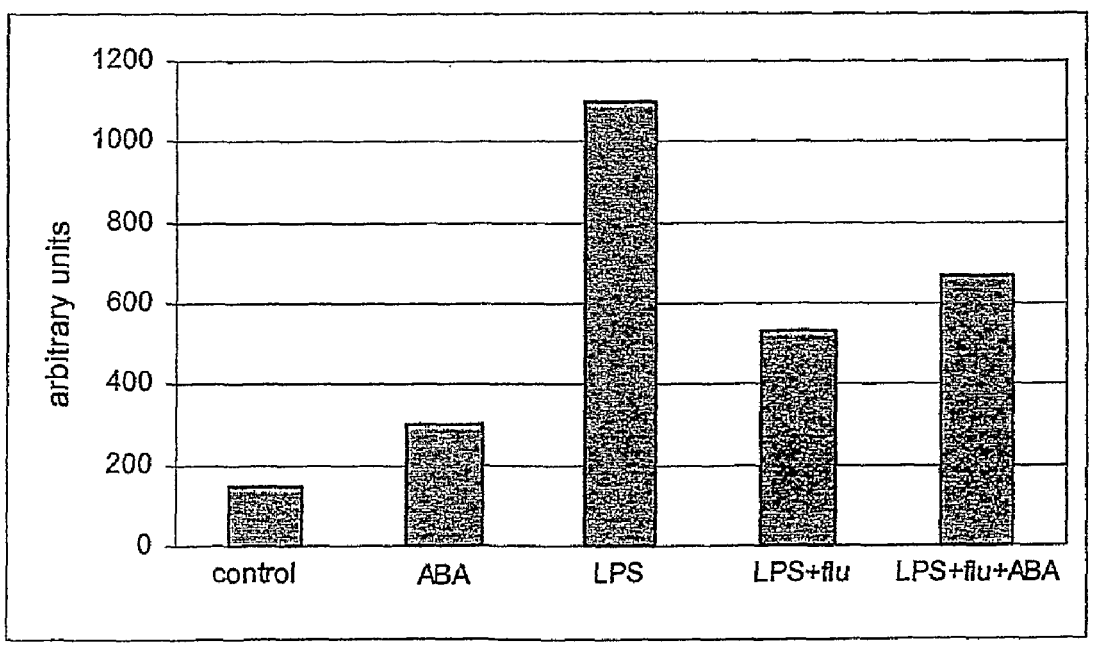

FIG. 11 shows the effects of ABA and of fluridone on COX-2 expression in the murine macrophages RAW 264.7 stimulated with LPS. Murine macrophages from the RAW 264.7 cell line were stimulated with 10 µM ABA or with 100 ng/ml lipopolysaccharide (LPS) for 6 hours, after pre-incubation with 50 µM fluridone for 3 hours.

EXPERIMENTAL SECTION

1. Pro-Inflammatory Effects of ABA on Blood Cells 1.1 Human Granulocytes and Lymphocytes.

Granlocytes were isolated by density gradient centrifugation from the peripheral blood of healthy donors, after informed consent. Contaminating erythrocytes were removed by hypotonic lysis. Addition to the granulocytes of ABA, at concentrations ranging from 0.2 to 200 µM, induces a dose-dependent stimulation of the cyclase activity (FIG. 1A), which is already detectable after 5 min, and a consequent increase of the intracellular cADPR concentration ([cADPR]$_i$) (FIG. 1B). The increase of [cADPR]$_i$ in turn induces a progressive rise of [Ca$^{2+}$]$_i$, from a basal value of 50±2 nM to 170±25 nM after 10 min from the addition of 10 µM ABA (n=4). The increase of [Ca$^{2+}$]$_i$ is partly inhibited (by approx. 60%) by 8-Br-cADPR (a specific cADPR antagonist) and by the inhibitor of inositol triphosphate synthesis (I-IP$_3$) and is completely abrogated by the concomitant presence of 8-Br-cADPR and I-IP$_3$, indicating that both cADPR and IP$_3$ are involved in the calcium response triggered by ABA. Extracellular EGTA almost completely prevents the increase of the [Ca$^{2+}$]$_i$ induced by ABA: this demonstrates that it is primarily due to calcium influx from the extracellular environment. cADPR-sensitive calcium channels have already been described on the plasmamembrane of human granulocytes. The increase of the [Ca$^{2+}$]$_i$ induced by ABA in granulocytes is in turn responsible for activation of several functional activities typical of these cells. The functional effects induced by ABA (at concentrations ranging between 0.2 and 20 µM) in granulocytes include stimulation of the production of reactive oxygen species (ROS), measured through the cytochrome c oxidation (FIG. 2A), and of nitric oxide (NO), measured as accumulation of nitrite, the end-product of NO reduction (FIG. 2B). Both effects are inhibited by 8-Br-cADPR, nicotinamide (an inhibitor of cyclase activity) and by EDTA, demonstrating the involvement of cyclase activity, cADPR and calcium in the functional responses induced by ABA. Finally, ABA triggers a significant increase of chemokinesis (cell movements not targeted towards an attractant) and behaves as a chemoattractant for granulocytes (FIG. 3). These functional responses are also inhibited by nicotinamide and by 8-Br-cADPR.

In conclusion, ABA triggers the following pathway of molecular events, which leads to activation of the "killing" function of these cells:

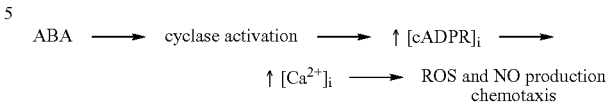

Lymphocytes were isolated by density gradient centrifugation from the peripheral blood of healthy donors, after informed consent. Addition of ABA to the lymphocytes, at concentrations ranging between. 50 and 500 µM, induces a slight (30%) yet statistically significant stimulation of the proliferation in the absence of other stimuli, such as phorbol myristate acetate (PMA) or phytohemagglutinin (PHA), which are usually required to induce proliferation in non-activated lymphocytes.

1.2 Human and Murine Monocytes/Macrophages

Monocytes were isolated by density gradient centrifugation from the peripheral blood of healthy donors, after informed consent, and were separated from lumphocytes by adhesion on tissue culture flasks. Addition of ABA, at concentrations ranging between 0.1 and 10 µM, induces an increased production of prostaglandin E$_2$ (PGE$_2$) (FIG. 4A), a cytokine with pro-inflammatory properties, through the increased expression of the enzyme cyclooxygenase 2 (COX-2), as detected by Western blot analysis and densitometric scanning of the protein band. Moreover, at the same concentrations, ABA induces also a significant increase of the release of the pro-inflammatory cytokine tumour necrosis factor-α (TNF-α) (FIG. 4B) and of the monocyte chemoattractant protein-1 (MCP-1) (approx. two-fold, FIG. 5), a known chemoattractant for monocytes and granulocytes.

The effects of ABA have also been studied on macrophages (activated monocytes) of murine origin. The same effects described above in human monocytes, i.e. increased release of PGE$_2$ and of TNF-α upon addition of ABA (0.1-10 µM), have been observed also on murine macrophages (the RAW 264.7 cell line) (FIGS. 6 A and B). Moreover, at concentrations ranging between 0.2 and 20 µM, ABA induces an increase of the release of NO and of TNF-α and an increase of chemokinesis similar to that observed on granulocytes also on the murine microglia cell line N9 (microglia is the macrophage population of the nervous tissue).

In conclusion, these results indicate that exogenously added ABA, at concentrations ranging between 0.2 and 20 µM, induces several pro-inflammatory effects on granulocytes, lymphocytes and human and murine monocytes, stimulating production of ROS, NO, PGE$_2$, TNF-α, stimulating lymphocyte proliferation and functioning as a chemoattractant for granulocytes.

2. Presence of ABA in Human Plasma and in Blood Cells 2.1 ABA in Plasma

The presence of ABA in human plasma was determined by HPLC-coupled mass spectrometry (HPLC-MS). ABA concentration in plasma is in the range of 5-10 nM, with presence of both the cis-trans isomer (the active form in plants), and of the trans-trans isomer. Presence of this isomer suggests ABA metabolism in humans.

2.2 ABA in Human Granulocytes and Lymphocytes

With the same HPLC-MS analysis, presence of ABA was also demonstrated in human granulocytes and lymphocytes freshly isolated from peripheral blood, at the concentration, respectively of 0.43±0.05 and 0.53±0.1 pMoles/mg proteins. Moreover, after stimulation of granulocytes for 18 hours with the synthetic chemoattractant peptide formil-Met-Leu-Pro (f-MLP), a known activator of granulocyte function, the intracellular ABA content doubled (0.84±0.1 pMoles/mg). Likewise, incubation of lymphocytes for 18 hours with PMA, a known lymphocyte activator, induced the doubling of the ABA content in these cells (1.1±0.4 pMoles/mg). Presence of ABA was determined by HPLC-MS also in other human cell types. The table below summarizes the results obtained.

| Cell type | ABA content pMoles/mg proteins |
| --- | --- |
| Granulocytes | 0.43 ± 0.05 (n = 3) |
| Lymphocytes | 0.53 ± 0.1 (n = 4) |
| Fibroblasts (skin) | 9.0 ± 0.1 (n = 3) |
| Mesenchymal stem cells (bone marrow stroma precursors) | 2.63 ± 0.3 (n = 3) |
| Platelets | 0.033 ± 0.01 (n = 3) |
| Monocytes | 12.96 ± 2.1 (n = 3) |

2.3 ABA in Murine Microglial Cells

The presence of ABA was also determined in the murine microglial cell line N9 (by HPLC-MS) and in this case too the hormone concentration increases more than 4 times after stimulation of the cells with bacterial lipopolysaccharide (LPS), a known activator of both monocytes and granulocytes, increasing from 0.3±0.05 to 1.3±0.2 pMoles/mg proteins (FIG. 8).

Presence of endogenous ABA in inflammatory cells, both in those isolated from peripheral blood and in cell lines, and the increase of the intracellular hormone concentration upon stimulation of cells with known pro-inflammatory agonists (f-MLP, PMA, LPS) suggest a physiological role of the hormone in the functions of these cells.

3. Effects of Fluridone on the Content of ABA and of Other Cytokines in Inflammatory Cells 3.1 Fluridone and ABA Content in Human Granulocytes and Lymphocytes The increase of the intracellular ABA concentration induced by f-MLP in granulocytes and by PMA in lymphocytes is inhibited by the addition of fluridone at micromolar concentrations (ranging between 10 and 50 µM) during cell incubation with the pro-inflammatory stimuli. In particular, a 40% and 50% inhibition was observed in granulocytes and in lymphocytes, respectively (data obtained with a commercially available immunoassay for ABA (Sigma).

3.2 Fluridone and ABA Content in Murine-Microglia Cells

In the murine microglia cell line N9 addition of fluridone (50 µM) together with LPS significantly reduced (by 60%) the increase of the intracellular ABA content induced by this pro-inflammatory stimulus (FIG. 8).

Altogether these results indicate that fluridone, at micromolar concentrations, is able to reduce the ABA content in human and murine inflammatory cells stimulated with known pro-inflammatory agonists. Since ABA itself has pro-inflammatory effects on these cell types (see above, paragraph 1) this observation suggests that the decrease in ABA content could be coupled to a reduced functional efficiency of the cells, as indeed was experimentally demonstrated (see paragraph 4).

3.3 Fluridone and Release of Inflammatory Cytokines by Human Monocytes

The effects of fluridone are not restricted to the decrease of ABA content (here described for the first time as an inflammatory cytokine). Some very interesting observations indicate an inhibitory effect of fluridone on the release of other already known inflammatory cytokines. Fluridone, at 50 µM, almost completely inhibits the release of MCP-1, a pro-inflammatory cytokine, by LPS-stimulated human monocytes (FIG. 8). MCP-1 released by activated monocytes is believed to be involved in the genesis of vascular re-stenosis after angioplasty, due to the stimulatory effects of this cytokine on the proliferation of vascular myocytes. Moreover, pre-incubation with 50 µM fluridone completely inhibits histamine release by LPS-stimulated (unfractionated) blood cells (FIG. 9).

These results indicate that fluridone could have broad spectrum anti-inflammatory effects, thanks to its ability to reduce both the ABA content and the production of other, already known cytokines in different cell types involved in inflammation.

4. Anti-Inflammatory Effects of Fluridone 4.1 Human Granulocytes and Lymphocytes Fluridone at 50 µM inhibits by approximately 80% the NO release by human granulocytes stimulated with 1 µM f-MLP, 10 µM β-amyloid or 100 µM ATP (all known activators of the release of this cytokine).

Pre-incubation of human lymphocytes with fluridone (50 µM) significantly inhibits (by 90% and 50%, respectively) cell proliferation induced by PMA and phytohemagglutinin (PHA), two known activators of lymphocyte proliferation (FIG. 10 A). Inhibition of proliferation is not due to fluridone toxicity since the percentage of viable cells (excluding the dye Trypan blue) was similar in the cultures incubated with fluridone compared to controls. The addition of excess exogenous ABA (500 µM) together with fluridone partly restores the proliferative response (by approximately 40%) (FIG. 10 B), suggesting that the effect of fluridone is due to inhibition of the endogenous ABA synthesis in lymphocytes.

4.2 Human and Murine Monocytes/Macrophages

Both in human monocytes and in murine macrophages of the continuous cell line RAW 264.7 incubation with 50 µM fluridone completely inhibits LPS-stimulated $PGE_2$-production (FIGS. 4 A and 6 A). A similar effect (90% inhibition) is produced by fluridone also on the LPS-induced TNF-α production in both cell types (FIGS. 7 A and B). In all these cases, no toxicity of fluridone on the cells was observed, as evaluated by the ability of excluding the dye Trypan blue. The addition of exogenous ABA (10-20 µM) to the cultures partly restores the cell function compromised by fluridone: TNF-α release in monocytes (FIG. 4 B) and in RAW cells (FIG. 6 B), the increase of COX-2 expression in LPS-stimulated RAW 264.7 (FIG. 11), NO and TNF-α release in microglia (FIGS. 7 A and B).

These observations, in addition to the similar one described in the previous paragraph for lymphocytes, suggest that the anti-inflammatory effects of fluridone on these cell types are due to inhibition of the endogenous synthesis of ABA.

The following table summarizes the main results described above.

| Cell type | Added ABA | Effects of ABA | Effects of Fluridone | Effects of Fluridone + ABA |
|---|---|---|---|---|
| Human lymphocytes | 50-500 µM | ↑proliferation | ↓PMA-, LPS-, PHA-induced proliferation | restoration (50%) PMA-, LPS-induced proliferation |
| Human granulocytes | 0.2-20 µM | ↑NO release<br>↑ROS release<br>↑chemokinesis<br>↑chemotaxis | ↓fMLP-, ATP-, β-amyloid-induced NO release | |
| Human monocytes | 5-50 µM | ↑COX-$PGE_2$<br>↑TNF-α release<br>↑MCP-1 release | ↓TNF-α release<br>↓COX-$PGE_2$<br>↓MCP-1 release | restoration (60%) TNF-α release |
| Murine microglia (N9) | 0.2-20 µM | ↑NO release<br>↑TNF-α release<br>↑chemokinesis | ↓NO release<br>↓TNF-α release | restoration (60%) NO and TNF-α release |
| Murine macrophages (RAW 264.7) | 0.1-10 µM | ↑COX-$PGE_2$<br>↑TNF-α release | ↓COX-$PGE_2$<br>↓TNF-α release | restoration (60%) TNF-α and $PGE_2$ release |

In conclusion, from the results presented, it is possible to conclude as follows:
  ABA added exogenously to human and murine inflammatory cells, at concentrations preferably ranging between 250 nM and 20 µM, induces stimulatory effects on typical functions of each cell type (lymphocyte proliferation, production of inflammatory cytokines by monocytes/macrophages, NO production and chemotaxis in granulocytes);
  Fluridone, at concentrations ranging between 5 and 50 µM, significantly decreases or abolishes the effects of chemical stimuli known to activate these pro-inflammatory functions in these cell types;
  addition of excess ABA together with fluridone partly restores the compromised function, suggesting a role for endogenous ABA in the regulation of these cell processes;
  ABA is indeed present in plasma and in the cell types listed above and its intracellular concentration is regulated in the same cells by known pro-inflammatory stimuli.

These results allow to state that ABA is a novel pro-inflammatory cytokine in humans and that fluridone, known in plant biology for its inhibitory effects on ABA synthesis in plants, possesses anti-inflammatory effects at micromolar concentrations. These concentrations could be reached in the blood of patients by administration of a quantity of fluridone around the ADI (acceptable daily intake) which is 0.08 mg/Kg/die in humans. Indeed, a plasma concentration of 5 µM is equivalent to 0.0016 mg/ml, i.e. 8 mg in 5 l blood, equivalent to 0.1 mg/Kg for an adult weighting 80 Kg.

Materials and Methods

Isolation of Blood Cells

Blood enriched in leukocytes (buffy coat), was provided by Galliera Hospital, Genova, Italy, upon informed consent of the volunteer donors. Lymphocytes, granulocytes and monocytes were isolated by density centrifugation through Ficoll-Paque (Amersham Biosciences, Uppsala, Sweden). Low-density mononuclear cells (including lymphocytes and monocytes) were collected at the plasma-Ficoll interphase and monocytes were further purified by adherence to plastic cell culture flasks. Granulocytes were isolated from high-density cells, sedimented under the Ficoll layer by hypotonic lysis of contaminating erythrocytes. All cell populations were then resuspended in RPMI 1640 medium (Sigma) containing penicillin (100 U/ml), streptomycin (100 µg/ml) and 20% autologous plasma. Culture conditions were as those described below for cell lines.

"In Vitro" Culture of Continuous Cell Lines

The cell lines of murine origin used in this study (RAW 264.7 macrophages, N9 microglia and L929 fibroblasts, used for the TNF-α assay) were cultured at 37° C. in the presence of 5% $CO_2$ in a medium containing DME (for RAW 264.7), RPMI (for L929) or IMDM (for N9) (all media were purchased from Sigma, Milano, Italia) supplemented with penicillin, streptomycin and fetal calf serum (10%) (Hyclone, Logan, Utah, USA).

Assays of GDP-Ribosyl Cyclase Activity and cADPR Content in Granulocytes

Granulocytes were resuspended in HBSS ($60 \times 10^6$/ml) and cyclase activity was measured by adding the substrate $NGD^+$ (a $NAD^+$ analogue, which product cGDPR is fluorescent) at the concentration of 0.2 mM together with increasing concentrations of ABA. At various times (0, 5, 15, 60 and 120 min) 100 µl-aliquots were withdrawn and centrifuged (5,000×g for 15 s) and supernatants were deproteinized with 2.5% (v/v) trichloroacetic acid. The cGDPR content was estimated by HPLC analysis, as described in (Guida, FEBS 1995).

The assays to determine the intracellular cADPR concentration ($[cADPR]_i$) in granulocytes are known to the expert in the field. Granulocytes ($40 \times 10^6$/ml in RPMI 1640) were incubated in the presence of 20 µM ABA and at various times 500 µl-aliquots were withdrawn and centrifuged (5,000×g for 15 s) to recover the cell pellets. Determination of the $[cADPR]_i$ was performed on perchloric acid cell extracts by an enzymatic cycling assay, as described in (Graeff, Biochem. J. 2002).

Colorimetric Assay for Nitrites and Nitrates

The method used to determine NO released from the cells into the medium exploits the spontaneous conversion of NO to nitrates and the subsequent enzymatic reduction of nitrates to nitrites by the enzyme nitrate reductase. Nitrites are revealed by the Griess reagent and their concentration is calculated from a standard curve of $NaNO_2$. Granulocytes ($60\times10^6$/well) or murine microglia cells N9 ($2\times10^5$/well) were incubated in 24-well plates for 60 min at 37° C. in the presence of ABA at different concentrations. The supernatants were then centrifuged and diluted with an equal volume of Griess reagent (0.1% naphthyl-ethylenediamine dihydrochloride in distilled water, 1% sulphanylamide in 5% concentrated $H_3PO_4$). Absorbance at 545 nm was estimated after 10 min and the nitrite concentration was calculated using a standard curve, generated in parallel with known amounts of $NaNO_2$.

Colorimetric Assay for Reactive Oxygen Species (ROS) Production

Release of superoxide ($O_2^-$) by human granulocytes was quantified by a spectrophotometric assay of cytochrome c reduction (Cohen, J Clin Invest 1978). Granulocytes were resuspended in HBSS (at $5\times10^6$ cells/ml) and 225 μl of the cell suspension was incubated for 30 min at 37° C. with 50 μl cytochrome c (0.2 mM) in the absence (control) or in the presence of ABA at different concentrations. Then, cells were centrifuged at 5,000×g for 15 s and the absorbance of the supernatants was recorded at 550 nm (λmax for reduced cytocrome c).

Assay for TNF-α and $PGE_2$ Production by Inflammatory Cells

The method used to assay TNF-α is based on the high sensitivity of the murine fibroblast cell line L929 to the toxic effect of this cytokine. Briefly, fibroblasts were seeded ($3\times10^4$/well) in 96-well plates and after 24 h the medium was substituted with the supernatant of the cell cultures where the TNF-α content was to be estimated. In parallel, known amounts of the cytokine were added to other wells, in order to obtain a standard curve of toxicity. After 48 hours, MTT (0.05 mg/ml) was added to each well and after 3 hours incubation at 37° C. (during this time viable cells reduce the dye producing formazan crystals), the medium was removed, DMSO (200 μl/well) was added to dissolve the formazan crystals and the absorbance was recorded at 570 nm with a spectrophotometric plate reader. The TNF-α concentration in the culture supernatants was calculated by comparison of the percentage of viable cells in the treated wells with those containing known amounts of TNF-α (standard curve). The $PGE_2$ release in the medium by stimulated inflammatory cells was measured by an immunoenzymatic assay kit, commercially available ($PGE_2$ EIA-kit, Cayman Chemicals, Ann Arbor, Mich., USA).

Chemotaxis and Chemokinesis

Assays were performed using 96-well ChemoTx system microplates with a 3-μm pore size polycarbonate filter (NeuroProbe Inc., Gaithersburg, USA). Cells (granulocytes or murine microglia) were resuspended at $10^7$/ml in HBSS, PBS and 5% albumin, 39:16:1 (chemotaxis buffer, CB). In order to evaluate the chemoattractant effect of ABA, hormone concentrations ranging from 50 nM to 20 μM were added in CB in the bottom wells and 25 μl cell suspensions were placed on top of the filter. To evaluate a possible stimulatory effect of ABA on spontaneous cell movements (chemokinesis), cells were pre-incubated with or without 20 μM ABA, then washed and placed on top of the filter, in contact with CB. Plates were incubated at 37° C. for 60 min and transmigrated cells were recovered and quantified by fluorimetric assay with Cytox Green. The number of transmigrated cells was calculated by comparison of the measured fluorescence with that of a standard curve, obtained by directly placing a serial dilution of cells in the bottom wells. The results of the chemotaxis experiments are expressed as "chemotaxis index" (CI):

CI=number of cells migrated towards chemoattractant/number of cells migrated towards CB The results of the chemokinesis experiments are expressed as number of ABA pre-treated cells migrated through the filter compared to control cells (not treated with ABA).

Detection of ABA Content in Murine Microglia Cells by HPLC-Coupled Mass Spectrometry.

N9 cells were seeded ($25\times10^6$/flask) in IMDM medium containing fetal calf serum, incubated for 3 h at 37° C. with or without 50 μM fluridone and then incubated for 3 days in the absence or in the presence of 200 ng/ml lipopolysaccharide (LPS). Cells were then recovered, washed in phosphate-buffered saline isotonic solution at pH 7.4 (PBS), resuspended in 0.5 ml water and sonicated. An aliquot from each cell lysate (10 μl) was used to assay protein content (using the method by Bradford), the rest was added to methanol (2 ml) and 1400 cpm [$^3$H]-ABA (Amersham, Milan, Italy) as internal standard. The acid extraction of ABA was performed in an apolar phase. A small aliquot of the extract was used to determine radioactivity (with a β-counter), allowing the calculation of the percentage of ABA recovery after-extraction. The rest of the extract was analyzed on an Agilent 1100 capillary chromatography system, with a diode array detector, equipped with a Waters Atlantis™ $dC_{18}$ 150×1 mm column, particle size 3 μm, coupled to an Agilent 1100 series LC/MSD Trap mass spectrometer, equipped with an orthogonal geometry electrospray source and ion trap analyser. The HPLC separation was performed at a flow rate of 30 μl/min, with buffer A (1% v/v acetic acid in water) and buffer B (90% acetonitrile and 10% buffer A) and the following gradient: from 0 to 3 min 100% A, from 3 to 35 min linearly increasing to 100% B, from 35 to 40 min 100% B. The detection wavelength was set at 254 nm. MS (ion 263.3) and MS/MS (ions 219.3; 153.4) spectra were acquired in negative ion mode in the m/z range 50-300. The intracellular ABA concentration was revealed by HPLC-MS analyses and was obtained by comparison of the area of its HPLC peak with the area of known amounts of ABA, injected separately and taking into consideration the percentage of recovery after extraction, as assessed with the radioactive tracer.

The invention claimed is:

1. Method for treating an inflammation in a patient, the method comprising
administering to said patient a therapeutically effective amount of a fluridone having formula:

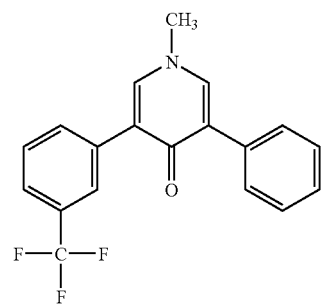

the therapeutically effective amount suitable to provide in the patient a blood concentration of fluridone comprised between 250 nM and 50 μM.

2. The method according to claim 1, wherein the fluridone is administered as an anti-inflammatory active compound in a medicament.

3. The method according to claim 2, wherein the fluridone is administered in a medicament comprising a pharmaceutically effective amount of fluridone and a pharmaceutically acceptable carrier or diluent.

4. The method according to claim 3, wherein the medicament is in a form suitable for systemic or topical administration.

5. The method according to claim 3, wherein the medicament is in a form suitable for oral, intravenous, intramuscular, subcutaneous, rectal, intradermal, nasal, tracheal or bronchial administration.

6. The method according to claim 3, wherein the medicament is in a dosage form selected from tablets, capsules, vials, suppositories, injectable solutions or suspensions, creams, lotions, colluttories, powders, and solutions.

7. The method according to claim 1, wherein fluridone is administered in a therapeutically effective amount suitable to provide a blood concentration comprised between 5 µM and 20 µM.

8. The method according to claim 1, wherein fluridone is administered in a therapeutically effective amount of at least 0.1 mg/kg body weight.

9. The method according to claim 8, wherein fluridone is administered in a therapeutically effective amount between 0.1 and 0.4 mg/kg body weight.

10. Method for administering fluridone, the method comprising:
administering fluridone having formula

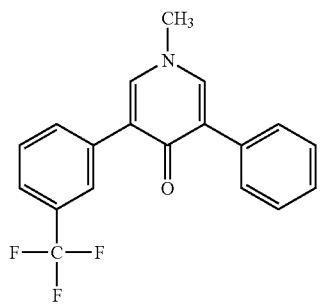

to a patient presenting an inflammation,
wherein the fluridone is administered to the patient in an amount suitable to provide a blood concentration comprised between 250 nM and 50 µM, and
wherein the administered amount is a therapeutically effective amount to treat the inflammation in the patient.

11. The method according to claim 10, wherein the fluridone is administered to the patient in an amount suitable to provide a blood concentration comprised between 5 µM and 20 µM.

12. The method according to claim 10, wherein the fluridone is administered to the patient in a therapeutically effective amount of at least 0.1 mg/kg body weight.

13. The method according to claim 10, wherein the fluridone is administered to the patient in a therapeutically effective amount of between 0.1 and 0.4 mg/kg body weight.

* * * * *